United States Patent [19]
Peters, M.D. et al.

[11] Patent Number: 5,108,898
[45] Date of Patent: Apr. 28, 1992

[54] USE OF FIBRONECTIN HAVING A VARIABLE INCLUDED TYPE III REPEAT SEQUENCE AS A MARKER FOR TOXEMIA IN PREGNANCY

[76] Inventors: John H. Peters, M.D., 3290-58 Via Marin, La Jolla, Calif. 92037; Charles J. Lockwood, M.D., 210 Hobart, Hingham, Mass. 02043

[21] Appl. No.: 298,622

[22] Filed: Jan. 18, 1989

[51] Int. Cl.$^5$ ............... G01N 33/53; G01N 33/542; G01N 33/68
[52] U.S. Cl. .................... 435/7.9; 435/7.92; 435/21; 436/518; 436/536; 436/86; 436/811; 436/815; 436/822; 436/87
[58] Field of Search ............ 435/79, 7.92, 21; 436/518, 536, 815, 86, 87, 811, 822

[56] References Cited
U.S. PATENT DOCUMENTS
4,980,279 12/1990 Peters et al. ............ 435/87

OTHER PUBLICATIONS
Atherton, B. T., et al., *Cell*, vol. 25, 133–141, Jul. 1981.
Hayashi, M., et al., *J. Biol. Chem.*, vol. 256, No. 21, 11292–11300, 1981.
Schwarzbauer, J. E., et al., *Proc. Natl. Acad. Sci. U.S.A.*, vol. 82, 1424–1428, 1985.
Kornblihtt, A. R., et al., *Nuc. Acids Res.*, vol. 12, No. 14, 5853–5868, 1984.

*Primary Examiner*—Esther L. Kepplinger
*Assistant Examiner*—Toni R. Scheiner
*Attorney, Agent, or Firm*—Douglas A. Bingham

[57] ABSTRACT

The elevation of human cellular fibronectin monomers having a variably included Type III repeat in a pregnant woman, as early as the first trimester, has been found to precede the onset of the clinical manifestations of toxemia and correlate with the severity of the disease state. The present invention provides a means of detection for and the monitoring of the toxemias of pregnancy, particularly preeclampsia and eclampsia, by the use a marker, human fibronectin having a variably included Type III repeat sequence, ED1 or ED2.

19 Claims, 1 Drawing Sheet

ED1

```
1                                              47
NIDRPKGLAFTDVDVDSIKIAWESPQGQVSRYRVTYSSPEDGIHELF
PAPDGEEDTAELQGLRPGSEYTVSVVALHDDMESQPLIGTQST
48                                             90
```

1 47
NIDRPKGLAFTDVDVDSIKIAWESPQGQVSRYRVTYSSPEDGIHELF
PAPDGEEDTAELQGLRPGSEYTVSVVALHDDMESQPLIGTQST
48 90

1 57
EVPQLTDLSFVDITDSSIGLRWTPLNSSTIIGYRITVVAAGEGIPIFEDFVDSSVGY
YTVTGLEPGIDYDISVITLINGGESAPTTLTQQT
58 91

USE OF FIBRONECTIN HAVING A VARIABLE INCLUDED TYPE III REPEAT SEQUENCE AS A MARKER FOR TOXEMIA IN PREGNANCY

This invention was made with the support of the U.S. Government, and the U.S. Government has certain rights in the invention pursuant to National Institutes of Health Contract GM-08172, HL-23584, GM-37696 and HL-28235.

TECHNICAL FIELD

The present invention relates to a method for the detection and monitoring of toxemia, particularly preeclampsia, in a pregnant woman by use of a marker, human fibronectin having a variably included Type III repeat (ED1+Fn or ED2+Fn). More specifically, it relates to a method for the determination of the concentration of the fibronectin in a body sample from a pregnant woman, which concentration has been found to correlate with the disease state.

BACKGROUND

Preeclampsia and eclampsia are toxemias associated with pregnancy. Preeclampsia is classically defined as the triad of hypertension, proteinuria, and edema associated with pregnancy. Other manifestations of preeclampsia are vascular prostenoid and platelet derangements, vasospasm, utero-placental vascular lesions, and in severe cases, convulsions and coma (eclampsia). Walsh et al., *Am. J. Obstet. Gynecol.*, 151:100-15 (1985); Goodman et al., *Am. J. Obstet. Gynecol.*, 142:817-22 (1982); Kitzmiller et al., *Am. J. Obstet. Gynecol.*, 118:362-8 (1974); Giles et al., Br. *J. Obstet. Gynecol.*, 88:1115-19(1981); and Gant et al., *J. Clin Invest.*, 52:2682-89 (1973).

Toxemia occurs more often in women pregnant for the first time and in those over the age of thirty-five. Toxemia is especially frequent in patients with prior renal and vascular disease. A significant percentage of pregnant women with preexisting hypertension are also likely to have a toxemic episode.

A common histologic finding in toxemia is a marked swelling of the endothelial and epithelial cells of the glomeruli of the kidneys. A characteristic lesion in toxemia is deposition of fibrin in the glomeruli. Harrisons, *Principles of Internal Medicine.* 7th ed., McGraw Hill Co., pgs 1401-02, (1974). The onset of toxemia may be insidious or quite abrupt. Although toxemia generally occurs in the third trimester, it may also begin much earlier.

Although the combination of abnormalities associated with preeclampsia suggests that the disorder may result from progressive maternal and/or placental endothelial-vascular damage, the lack of specific markers for endothelial-vascular injury has prevented testing this hypothesis. A marker that correlates with the disease state and that indicates preeclampsia prior to clinical evidence of the disease would allow detection of preeclampsia early in the course of the disease when clinical intervention can be effective or possibly preventative.

Fibronectin, fibrinogen, antithrombin III, fibrin monomer, $(\alpha)_2$-antiplasmin, fibrinogen split products and D-dimer have been studied to determine their value as predictive markers. Elevated levels of total circulating (plasma) fibronectin, as compared with controls, have been observed in preeclamptic patients late in gestation. Stubbs et al., *Am. J. Obstet. Gynecol.*, 150(7):885-87 (1984); Lazarchick et al., *Am. J. Obstet Gynecol.*, 154(5):1050-53 (1986); and Saleh et al., *Am. J. Obstet. Gynecol.*, 157 (2): 331-336, (1987). Fibronectin is an adhesive glycoprotein found in plasma and on cell surfaces and extracellular matrices. By binding other macromolecules as well as cells, fibronectin serves to promote anchorage of cells to substrata. Hynes, in *Cell Biology of the Extracellular Matrix*, Hay ed., Plenum Press, pages 295-334 (1982); Hynes et al., *J. Cell Biol.*, 95:369-77 (1982). Fioronectin has been observed to accumulate at sites of tissue injury in vivo. Peters et al., *Am. Rev. Resoir. Dis.*, 138:167-174, (1988).

Fibronectin is composed of subunits of variable primary structure [average relative molecular mass of 250 kilodaltons (kDa)]. The subunits are, disulfide-linked to form dimers or multimers derived from a pool of similar but nonidentical polypeptides. Hynes, in *Cell Biology of the Extracellular Matrix*, Hay ed., Plenum Press, pages 295-334 (1982); Hynes et al., *Cell Biol.*, 95:369-77 (1982); Schwarzbauer et al., *Proc. Natl., Acad. Sci. USA*, 82:1424-28; Kornblihtr et al., EMBO J., 4(7): 1755-59 (1985). Thus, fibronectin refers to several species of glycoprotein, some of which are more fully characterized than others.

Two major fibronectin classes are plasma fibronectin and cellular fibronectin. Plasma fibronectin (pFn) is secreted by hepatocytes, whereas cellular fibronectin (cFn) is secreted by a variety of cultured cells including endothelial cells and fibroblasts. Jaffe et al., *J. Exp Med.*, 147:1779-91 (1978); Birdwell et al., *Biochem. Biophys. Res. Commun.*, 97(2):574-8 (1980). Despite extensive physical and immunologic similarities, the two classes of fioronectin differ in electrophoretic behavior, solubility, and biologic activities. Tamkun et al., *J. Biol. Chem.*, 258 (7):4641-47 (1983); Yamada et al., *J. Cell Biol.*, 80:492-98 (1979); Yamada et al., Biochemistry, 16 (25) 2552-59, (1977).

Primary structural differences between plasma and cellular fibronectins have been found by peptide mapping [Hayashi et al., *J. Biol. Chem.*, 256(21):11,292-11,300 (1981)] cDNA cloning [Kornblihtt et al., Embo J., 4:1755-1759 (1985)] and immunologic techniques [Atherton et al., Cell, 25:133-41 (1981)]. From these data, it has been determined that the primary structure of fibronectin monomer contains three different types of internal repeats known as homology Types I, II and III, having length of about 40, 60 and 90 amino acids residues, respectively [Kornblihtt et al., *Embo J.*, 4:1755-1759 (1985)]. All of the various distinct Fn moieties are produced by a single gene, with differences in primary structure resulting from alternative splicing of the primary mRNA transcript in at least three regions. Kornblihtt et al., *EMBO J.*, 4(7):1755-59 (1985); Schwarzbauer et al., *Proc. Natl. Acad. Sci. USA*, 82:1424-28 (1985); Gutman et al., *Proc. Natl. Acad. Sci. USA*, 84:7179-82 (1987); Schwarzbauer et al., *EMBO J.*, 6(9):2573-80, (1987).

A variable region corresponding to a single exon, encoding for exactly one 90 amino acid Type III structural repeat was identified in mRNA from human fibroblasts and two human tumor cell lines, but could not be detected in human hepatocyte mRNA. The region was termed EDI ("ED" for extra domain). Kornblihtt et al., *EMBO J.*, 4(7):1755-59 (1985); Kornblihtt et al., *EMBO J.*, 3(1):221-26 (1984); Kornblihtt et al., *Nucleic Acids Res.*, 12(14):5853-68 (1984).

Since the vast majority of soluble Fn in the circulation is derived from hepatocytes [Tamkun et al., *J. Biol.*

Chem., 258(7):4641-47 (1985)], pFn is believed to be composed primarily of dimers comprised of Fn monomers lacking the ED1 region (ED1-monomers). Peters et al., *Amer. Rev. Reso. Dis.*, 138(1):167-74 (1988).

In contrast, the extra Type III repeat (ED1) was postulated to be a domain unique to cellular fibronectins. Shwarzbauer et al., *Proc. Natl. Acad. Sci. USA*, 82:1424-28 (1985); Kornblihtt et al., *EMBO J.* 3(1):221-26 (1984); Kornblihtt et al., *Nucleic Acids Res.* 12(14):5853-68 (1984). These cFns are produced by a variety of other cell types in the form of dimers or insoluble multimers, Schwarzbauer et al., *EMBO J.* 6(9):2573-80 (1987).

Recently Gutman et al., *Proc. Natl. Acad. Sci. USA*, 84:7179-82 (1987) reported a second region of Type III variability in human fibronectin that arises due to alternative RNA splicing. This region has been labelled ED2, for extra domain 2. The ED2 region is a 91 amino acid repeat having Type III homology and is located between the DNA- and the cell-binding domains of Fn as contrasted to the ED1 region located toward the C terminus of the molecule. Because hepatocytes are not known to produce mRNA having the variably included Type III sequences, both the ED1 and ED2 regions are restricted to cellular Fn.

Combination of all the possible patterns of splicing in these regions of variability can potentially lead to a large number of distinct Fn polypeptide monomers from a single gene. Schwarzbauer et al., *EMBO J.*, 6(9):2573-80 (1987), reports that an additional Type III repeat of Fn (III-9) could also potentially be variably included through alternative splicing of Fn RNA in certain cell lines.

BRIEF SUMMARY OF THE INVENTION

It has now been discovered that, as early as the first trimester of pregnancy, pregnant women destined to develop preeclampsia have an elevated level (concentration) of soluble fibronectins containing variably included Type III repeat, i.e., ED1 or ED2, in comparison to the level in women in the same stage of pregnancy who do not develop toxemias.

Thus, the present invention contemplates a method for detection and monitoring of toxemia, particularly preeclampsia, in a pregnant woman. The method comprises determining the concentration of fibronectin having a variably included Type III repeat (ED1 or ED2) in a body fluid sample from the pregnant woman. The method can be used to determine those patients destined to develop preeclampsia prior to the onset of maternal signs and symptoms of the disease when clinical intervention can be effective.

In particular, in comparison to controls, patients destined to develop preeclampsia had significant elevations in the concentration of fibronectin having a variably included Type III repeat sequence, referred to herein as ED+ Fn. Elevated ED+ Fn concentrations preceded the onset of maternal signs and symptoms of distress and correlated with the severity of the disease state.

The concentration of ED+ Fn can be readily determined by immunoassay at any time during the pregnancy and used to diagnose preeclampsia as early as the first trimester. This early detection of preeclampsia would allow for early therapeutic intervention. Further, the disease course can be followed by continued monitoring of the ED+Fn concentration.

BRIEF DESCRIPTION OF THE DRAWINGS

In the drawings that constitute a portion of this disclosure:

FIG. 1 illustrates the 90 amino acid sequence of the ED1 domain of fibronectin; and FIG. 2 illustrates the 91 amino acid sequence of the ED2 domain of fibronectin.

DETAILED DESCRIPTION OF THE INVENTION

The present invention contemplates a method for detection and monitoring of toxemia, particularly preeclampsia, in a pregnant woman. The method comprises determining the concentration of soluble fibronectin having a variably included Type III repeat (ED1 or ED2) in a body sample from the pregnant woman.

It has now been found that in comparison to controls, patients who developed preeclampsia had significant elevations in the concentration of soluble fibronectin having a variably included Type III repeat sequence, i.e., ED1+ Fn or ED2+ Fn, collectively referred to herein as ED+ Fn. Elevated ED+ Fn concentrations preceded the onset of maternal signs and symptoms of preeclampsia. Further, the concentrations correlated with the severity of the disease state.

The concentration of ED+ Fn can be readily determined by immunoassay at any time during the pregnancy and used to monitor pregnant women, at a preclinical stage, for eventual progression to preeclampsia. The assay can be performed on a routine basis during the first or second trimester in all pregnant women to warn physicians of impending preeclampsia. This early detection of preeclampsia would allow for therapeutic intervention prior to the onset of maternal signs and symptoms of preeclampsia. In women with an increased risk for preeclampsia, the test can be repeated at intervals during the pregnancy, preferably at least once during the second trimester. Further, continued monitoring of the ED+ Fn concentration can guide therapeutic intervention prior to or during the course of clinically evident disease.

A body fluid sample for the ED+ Fn assay can be obtained from a patient who may be at risk for toxemia at an early time point during the pregnancy, preferably within the first trimester. If the ED+ Fn concentration is in the normal range, an additional sample can be assayed at a later time to ensure the ED+ Fn concentration has remained normal. However, if the concentration is elevated in comparison to a control value, the patient can be treated to prevent the onset of preeclampsia. Thereafter, repeated analysis of ED+ Fn concentrations allows the physician to follow the disease course.

Abbreviations and Definitions

A. Definitions

Amino Acid: All amino acid residues identified herein are the natural L-configuration. In keeping with standard polypeptide nomenclaturs, *J. Biol. Chem.*, 243:3557-59 (1969), abbreviations for amino acid residues are shown in the following Table of Correspondence:

| Table of Correspondence | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

It should be noted that all amino acid residue sequences are represented herein by formulae whose left to right orientation is in the conventional direction of amino-terminus to carboxy-terminus.

As used herein the term "cellular fibronectin" or "cFn" refers to a fibronectin monomer having a variably included Type III repeat. The IIICS (Type III connecting segment) described by Kornblihtt et al., *EMBO*, 4(7):1755-59, (1985) and Gutman et al., *Proc. Natl. Acad. Sci. USA*, 84:7179-82 (1987) is not a "variably included Type III repeat. The known "variably included Type III repeat(s)" regions reported to date are ED1 and ED2. The amino acid residue sequence of ED1 and ED2 are illustrated in FIGS. 1 and 2, respectively. Thus, as used herein, cellular fibronectin encompasses a fibronectin monomer which contains at least one of the ED1 or ED2 domains, for example, ED2+ ED1+, ED2− ED1+, and ED2+ ED1−. The abbreviation "ED+ Fn" will also be used herein to designate a fibronectin monomer having at least one of the ED1 or ED2 domains. Those fibronectin monomers are produced by endothelial or fibroblast cells and are generally referred to as cellular fibronectin(s) in the art.

The term "plasma fibronectin" or "pFn" refers to the type of fibronectin monomer which is normally produced by hepatic cells and lacks the ED1 and ED2 domains.

The term "total fibronectin" as used herein, refers to the sum of all types of fibronectin monomers and includes pFn and ED+ Fn.

The term "antibody" in its various grammatical forms as used herein refers to a composition containing a population of immunoglobulin molecules and/or immunologically active portions of immunoglobulin molecules, i.e., molecules that contain an antibody combining site, including those portions known in the art as Fab, Fab', F(ab')2 and F(v).

The term "immunoreact" in its various forms means binding between an antigenic determinant-containing molecule and a molecule containing an antibody combining site such as a whole antibody molecule or a portion thereof.

Methods

A method for determining the amount or concentration of fibronectin having a variably included Type III repeat (ED+ Fn) in a body fluid sample comprises the following steps. A body fluid sample is obtained from a pregnant woman. The sample can be urine, serum or plasma, preferably serum or plasma.

An admixture is formed by admixing a predetermined amount of the a body sample with an antibody that immunoreacts with fibronectin having a variably included Type III repeat (ED+ Fn), but does not immunoreact with plasma fibronectin (pFn). The admixture is maintained for a time period sufficient for any ED+ Fn present in the sample to immunoreact with the antibody to form an immunoreaction product. The amount of immunoreaction product produced, and thus the amount of ED+ Fn in the sample, is determined. Various detection methods for quantitating the amount of immunoreaction product formed are well known.

Various heterogeneous and homogeneous assay protocols can be employed, either competitive or non-competitive. Numerous well known immunoassay formats can be used. Solid phase assays, such as enzyme-linked immunosorbent assays (ELISA), radio-labeled immunosorbent assays (RIA) or fluorochrome-linked immunosorbent assays (FIA) are particularly useful. The ELISA technique is preferred and is utilized herein as exemplary.

An antibody used in he present method immunoreacts with a fibronectin monomer having a variably included Type III repeat region but does not immunoreact with fibronectin monomers lacking those regions, i.e. plasma fibronectin. The antibody can be polyclonal or monoclonal. The antibody will usually immunoreact with native ED+ Fn. However, the use of antibodies that immunoreact with denatured ED+ Fn find use in methods that quantitate the denatured protein. The antibodies will preferably immunoreact with the ED1 region.

Methods of preparation of polyclonal and monoclonal antibodies specific for a particular protein are well known and include the use of the protein or of polypeptides that correspond to the amino acid residue sequence of a portion of the protein as the antigen in an immunogenic composition.

Polyclonal anti-ED+ Fn antibodies will usually be purified, as by immunoadsorption, to ensure the antibody composition has the required specificity. Generally, either the immunoadsorbent will contain pFn to remove anti-pFn antibodies from the composition or will contain ED1 or an ED1 region polypeptide to bind the desired antibodies. Immunoadsorption techniques which selectively bind and isolate the desired antibodies or remove antibodies specific for irrelevant antigens are well known. For a general review, see Goding, *J. Monoclonal Antibodies: Principle and Practice*, Academic Press, (1983).

Antibodies specific for the ED1 region of fibronectin have been produced. Anti-ED1 antibodies were induced by a polypeptide whose sequence corresponds to the portion of the ED1 domain from about amino acid residue position 35 to about position 61, as described in Peters et al., *Amer. Rev. Reso. Dis.*, 138(1):167-74 (1988); and Peters et al., *J. Clin. Invest.*, 78:1596-1603, (1986). The preparation of antibodies described therein is discussed in detail in the Examples and is used herein as exemplary.

Preferred polypeptides are those whose amino acid residue sequence substantially corresponds to a) ELFPAPDGEEDTAELQC,
b) ELFPAPDGEEDTAELQCGC,
c) TYSSPEDGIHELFPAPDGEEDTAELQC, or
d) TYSSPEDGIHELFPAPDGEEDTAELQCGC.

Monoclonal antibodies have also been produced using native cellular Fn. Keen et al., *Mol. Biol Med.,* 2:15-27 (1984); and Borsi et al., *J. Cell Biol.,* 104:595-600, (1987). Those articles are incorporated herein by reference. Thus, preparation of antibodies that distinguish ED-containing fibronectin monomers from plasma fibronectin monomers are well known.

In a preferred embodiment, the assay will be a solid phase assay in which the anti-ED+ Fn antibodies are affixed to a solid support. Numerous solid supports are known. A polystyrene or polyvinylchloride microtiter plate is preferred. The anti-ED+ Fn antibodies can be affixed to the solid support by well known techniques.

A predetermined amount of the body fluid sample is admixed with the solid support to form a solid-liquid phase admixture. Usually, for serum or plasma samples, the sample will be diluted about 1:10 to about 1:20 in an aqueous medium such as PBS or PBS/BSA prior to admixture with the antibodies.

That solid-liquid phase admixture is maintained for a period of time sufficient for any ED+ Fn present in the sample to immunoreact with the solid support-affixed antibody to form a solid phase-bound immunoreactant, and a liquid phase depleted of ED+ Fn. Maintenance (incubation) times typically range from about 1 to about 6 hours at room temperature (about 20° C.) to about 40° C.

The solid and liquid phases are then separated, conveniently by rinsing, to remove any unbound materials. The amount of solid phase-bound immunoreactant formed, and thus amount of ED+ Fn in the sample is then determined. Any of a number of well known techniques can be used.

The amount of solid phase-bound immunoreactant is conveniently determined by admixing a specific binding agent, a second antibody, that immunoreacts with the immunoreaction product to form a complex. Usually, the second antibody immunoreacts with bound ED1+ Fn, such as polyclonal or monoclonal anti-plasma fibronectin antibodies. The second solid-liquid phase admixture is maintained for a time period sufficient for the second antibody to immunoreact with the solid phase-bound human ED+ Fn and form a complex. The solid and liquid phases are again separated, and the amount of complex formed is determined.

Conveniently, the second antibody will be a labeled antibody. However, where the solid support affixed antibodies and the second antibody antibodies are induced in different animal species, such as in a goat and rabbit, the amount of second antibody in the complex can be determined using labeled third antibody, such as a labeled goat anti-rabbit IgG antibody.

A number of labels for use in immunoassays are well known and include radiolabels, flurochrome, dyes and enzymes. Typically used enzyme labels, such as horseradish peroxidase, β-galactosidase and alkaline phosphatase, are commercially available from a number of sources, as are the color-forming reagent(s). Enzyme-labeled anti-IgG antibodies specific for rabbit, goat or mouse IgG are also commercially available.

Detection limits in the assay have been found to be about 0.02 micrograms per milliliter of sample or about 1 nanogram per sample well for ED1+ Fn. To obtain those detection limits, non-specific binding sites on the solid supports are preferably blocked as by use of bovine serum albumin (BSA) prior to addition of sample.

As described herein and demonstrated in the Examples, concentrations of ED+ Fn, in particular serum or plasma concentrations of ED1+ Fn, are useful as a preclinical indicator of toxemia. More particularly, clinical signs of preeclampsia were preceded by accumulation in the circulation of ED+ Fn, specifically ED1+ Fn.

The two populations studied, women with normal pregnancies and women who developed preeclampsia, had no significant differences in maternal demographic criteria or gestational age at sampling. However, fibronectin concentrations were significantly different in the two populations as shown in Table II in the Examples. ED1+ Fn concentrations were greater in the preeclamptic patients overall and during each trimester of pregnancy, whereas total circulating Fn concentrations were significantly elevated in preeclamptic patients overall, and during the second and third, but not the first, trimesters.

The correlation of ED1+ Fn levels with hypertension and proteinuria demonstrated herein confirm the pathological relevance of its release. Additionally, increased ED1+ Fn concentrations with advancing gestational age, even in unaffected patients, has now been demonstrated. Although elevations in total circulating levels of Fn in preeclamptic patients have been reported, given the relatively small fraction of circulating Fn contributed by ED1+ Fn even among preeclamptic patients (less than 2%), it is clear than Fn lacking the ED1 (ED1−Fn) was the principal moiety detected in those studies. Further, the elevation of total circulating Fn observed in this study occured later in gestation than the elevation in ED1+ Fn and did not correlate with disease activity.

Thus, ED+ Fn concentration can be used to detect and monitor toxemias of pregnant women.

The following examples are intended to illustrate, but not limit the present invention.

EXAMPLES

Materials and Methods

Patients: Informed consent was obtained and citrated plasma samples were collected from 737 patients undergoing phlebotomy during routine obstetrical care at the Yale-New Haven Hospital obstetrical clinic. The samples were stored on ice, centrifuged at 5000 rpm for 10 minutes and stored at −70° C. Thirty-three patients were selected that met the following criteria for a preeclamptic condition: a 30 mm Hg rise in systolic blood pressure and/or a 15 mm Hg rise in diastolic pressure, associated with 1 gram/liter of proteinuria on at least two occasions greater than 6 hours apart. Thirty-six control patients were selected having a gestational age at sampling comparable to the preeclamptic patients, and were subsequently selected for comparable maternal age, race, parity, and smoking history. Exclusion criteria included maternal diabetes, chronic hypertensin, abruption, or infectious disease as well as multiple gestations and incomplete medical records.

Outcome variables: These included birth weight, gestational age at delivery, apgar scores, intrapartum mean arterial pressures, maximum proteinuria (Labstick, Miles Inc., Elkhart, In.), as well as the lowest platelet count.

Statistical analysis: Differences in continuous variables between the two groups were assessed by t-test. Multiple stepwise logistic regression was employed to determine the extent of correlation between Fn concentrations and outcome variables.

Preparation of anti-human fibronectin ED1 and anti-plasma fibronectin antibodies: Antibodies were prepared as described in Peters et al., *J. Clin. Invest.*, 78:1596–1603 (1986). The 90 amino acid ED1 domain of human fibronectin contains a region occurring at about position 35 to about position 61 amino acid residues from its amino-terminal end in which there is a relative absence of sequence homology with other Type III repeats. Kornblihtt et al., *EMBO J.*, 4(7):1755–59 (1985). A 29 amino acid residue polypeptide having the sequence, from left to right and in the direction from amino-terminus to carboxy-terminus, TYSSPEDG-IHELFPAPDGEEDTAELQGGC was synthesized using a solid phase methodology on an Applied Biosystems Model 438 peptide synthesizer (Applied Biosystems, Foster City, CA). Merrifield, *J. Am. Chem. Soc.* 85:2149–54 (1963). The N-terminal 27 amino acids of that polypeptide correspond to the region of ED1 amino acid residues located from 35 to 61 amino acids from its amino-terminus. The carboxy terminal glycine and cysteine were added for linkage to the solid phase during synthesis. A 19 amino acid residue polypeptide having a sequence from left to right and in the direction amino-terminus to carboxy terminus, ELFPAPD-GEEDTAELQGGC may be similarly produced by the procedure illustrated above. Peters et al., *J. Clin. Invest.*, 78:1596–1603 (1986).

Antibodies to rabbit plasma fibronectin (pFn) were raised in a goat by weekly multiple intradermal injections of 100 micrograms of purified antigen emulsified in Freund's adjuvant (Difco Laboratories, Detroit, MI.). Preparation and immunopurification of the anti-pFn antibodies was described in Peters et al., *Am. Rev. Respir. Dis.*, 138:167–174 (1988).

Antibodies to the ED peptide were similarly raised in goats by weekly intradermal injections in adjuvant of 150 micrograms of the ED peptide coupled to keyhole limpet hemocyanin (Pacific Bio-Marine, Venice, CA) by the glutaraldehyde method. Dockray, *Regulatory Peptides*, 1:169–86 (1980). The resulting goat anti-peptide antibodies were immunopurified as described in Peters et al., *Am. Rev. Resoir. Dis.*, 138:167–74 (1988). Antibody titers specific for the ED peptide were checked by ELISA. Engvall et al., *Arch. Biochem. Biophys.*, 222(2):649–58, (1983).

Measurement of Fn concentrations in plasma samples: A dual ELISA method for simultaneous measurement of ED1+ Fn and total Fn in samples of plasma was performed as described in Peters et al., *Am. Rev. Respir. Dis.*, 138:167–74 (1988) with the modifications as indicated below. Human cellular Fn derived from the media of human GM-1380 fibroblasts grown in Fn depleted media was utilized in place of rabbit fibroblast cellular fibronectin standards as a common standard for the ED1+ Fn and total Fn assays. Prior to ELISA assays, EDTA was added to each citrated plasma sample to give a final concentration of 5 mM. All assays were performed blinded to the patient's history.

Briefly, the ELISA method for ED1+ Fn was performed as follows. Fifty microliters ($\mu$l) of immunopurified goat anti-ED1+ Fn polypeptide antibodies at 8 micrograms per milliliter ($\mu$/ml) in 0.1M NaHCO: were pipetted into wells of 96 well flat-bottomed microtiter plates (Nunc, Kamstrup, Denmark) and incubated in a moist chamber for about 12–18 hours at room temperature. The wells were then washed twice with wash buffer (0.9 percent NaCl with 0.05 percent Tween 20), followed by incubation with 150 $\mu$l per well of a 2 percent BSA (bovine serum albumin) in 0.1 M NaHCO$_3$ at 37 degrees for about 2 hours. The wells were again washed twice with wash buffer, the excess buffer removed and then 25 $\mu$l of incubation buffer (PBS, pH 7.2, containing 0.3% Tween 20) was added to each well prior to the addition of standards or samples (in duplicate) diluted as indicated below. Fifty $\mu$l of fibroblast-derived ED1+ Fn standards or patient's plasma samples were diluted in BSA/EDTA solution (2 percent BSA in PBS and 1 mM EDTA) and then applied to duplicate wells and maintained (incubated) at 37° C. for about 3 hours. The plasma samples that were assayed for ED1+ Fn were diluted 1:16 and the plasma samples assayed for total fibronectin were diluted 1:2016. The fibroblast-derived ED1+ Fn standards that were assayed for ED1+ Fn were diluted over a range of 10 to 0.0137 $\mu$g/ml and the standards that were assayed for total fibronectin were diluted over a range of 3.3 to 0.0046 $\mu$g/ml.

The maintained wells were then washed 3 times with wash buffer, excess buffer was removed, and 50 $\mu$l of immunopurified goat anti-rabbit pFn antibodies, conjugated to alkaline phosphatase (Type VII from calf intestinal mucosa; Sigma Chem. Co.) by the glutaraldehyde method (Engvall et al., *Methods Enzymol.* 70:419–439, 1980) and diluted 1:250 in incubation buffer from the stock solution, were admixed with each well. The admixture was then maintained at room temperature for about 18 hours. Thereafter, the wells were washed and 100 $\mu$l of para-nitrophenyl phosphate diluted to 1 mg/ml in 1 M diethanolamine buffer, pH 9.8, was added to each well. The wells were then maintained for 25 minutes at room temperature to allow formation of a detectable color reaction product, and then 100 $\mu$l of 2M NaOH was added to the wells. The optical density of the colored reation product-containing solution was measured in a Bio-Tec micro plate reader (Bio-Tec Instruments, Inc., Burlington, VT) at 405 nm.

A cubic spline curvefitting program was run to generate standard curves in which the optical density of the colored solution is proportional to the log of the concentration of fibronectin standards. Coincubation of standard dilutions of cellular fibronectin with ED1 peptide at 33 $\mu$g/ml ablated the optical signal in the assay for ED1+ Fn but not in the assay for total fibronectin described hereinbelow, indicating that the former assay exclusively measures cellular fibronectin having a variably included Type III domain (ED1).

The ELISA for total Fn was performed essentially as described above for ED1+ Fn, using the above indicated cFn dilutions as standards and the same anti-pFn-alkaline phosphatase conjugate for the indicator antibody, but using immunopurified goat anti-pFn antibodies in place of the anti-ED1+ Fn antibodies. For small numbers of samples, the two assays can be performed on the same 96-well plate.

Study of Preeclamptic Patient's Fibronectin Levels

The two populations (normals and preeclamptic patients) have no significant differences in maternal demographic criteria or gestational age at the time of sampling (Table I).

TABLE I

Characteristics of Control and Preeclamptic (PE) Populations

| Variable Name | Control pop. mean (95% CI) n | PE pop. mean (95% CI) n | p = |
|---|---|---|---|
| Maternal age (yr) | 21.2 (22.0,22.4) 36 | 19.2 (18.2,20.9) 33 | 0.06 |
| Parity | 0.58 (0.26,0.91) 36 | 0.30 (0.02,0.59) 33 | 0.20 |
| GA draw (wk) | | | |
| overall* | 20.4 (18.9,22.8) 36 | 21.5 (18.7,24.3) 33 | 0.54 |
| 1st Tri. | 10.5 (8.7,12.3) 8 | 10.7 (8.8,12.5) 6 | 0.77 |
| 2nd Tri. | 21.6 (19.7,23.5) 26 | 21.3 (18.8,23.8) 20 | 0.83 |
| 3rd Tri. | 32.3 (28.1,36.3) 5 | 31.4 (29.7,33.1) 10 | 0.59 |

*overall gestational age at fibronectin sampling includes only last sample drawn in patients with multiple samplings.
CI = confidence interval Six patients had multiple sampling, three in each group. The overall racial distribution was 72% black, 14% hispanic and 13% white with no significant differences between the groups. Less than 10% of the patients in both groups smoked cigarettes.

Concentrations of total Fn and ED1+ Fn were significantly different in the two populations (Table II).

TABLE II

Plasma Concentration of ED1 + and Total Fibronectin in Control and Preeclamptic (PE) Populations

| Fibronectin Moiety | Control pop. mean (95% CI) n | PE pop. mean (95% CI) n | +p = |
|---|---|---|---|
| ED1 + Fn Conc. ug/ml | | | |
| overall* | 3.2 (2.9,3.6) 36 | 5.9 (4.8,7.0) 33 | .000 |
| 1st Tri. | 2.7 (2.2,3.2) 8 | 3.6 (2.8,4.5) 6 | .03 |
| 2nd Tri. | 3.2 (2.8,3.6) 26 | 5.8 (4.7,6.8) 20 | .000 |
| 3rd Tri. | 3.8 (2.5,5.2) 5 | 8.1 (5.11,2) 10 | .012 |
| Total Fn Conc. ug/ml | | | |
| overall* | 327 (306,348) 36 | 394 (360,427) 33 | .001 |
| 1st Tri. | 347 (283,411) 8 | 393 (334,451) 6 | .25 |
| 2nd Tri. | 316 (292,340) 26 | 380 (334,426) 20 | .016 |
| 3rd Tri. | 325 (250,400) 5 | 456 (366,546) 10 | .016 |

*overall concentrations of fibronectin represent only last sample drawn in patients with multiple samplings
CI = confidence interval
+ student's t-test ED1+ Fn concentrations were greater in the preeclamptic patients overall and greater during each trimester of pregnancy as compared to the control group. The total circulating Fn concentrations were also significantly elevated in preeclamptic patients overall, most notably during the second and third trimesters but not during the first trimester.

Regression analysis demonstrated that ED1+ Fn but not the total Fn concentrations significantly correlated with mean arterial pressure in labor (R=0.43, p=0.016), the degree of proteinuria (R=0.59, p=0.001) and the gestational age at sampling (R=0.49, p=0.000). Neither total Fn nor ED1+ Fn correlated with fetal distress (as determined by differences in one or five minute apgar scores), low birth weight or low platelet count.

Thus, as demonstrated in the study, ED+ Fn concentrations are useful to detect and monitor the toxemias of pregnancy.

The present invention has been described with respect to preferred embodiments. It will be clear to those skilled in the art that modifications and/or variations of the disclosed subject matter can be made without departing from the scope of the invention set forth herein.

What is claimed is:

1. An assay method for determining the amount of fibronectin having a variably included Type III repeat region in a sample comprising the steps of:
   (a) forming an immunoreaction admixture by admixing a predetermined amount of body fluid sample from a pregnant woman with an antibody that immunoreacts with fibronectin having a Type III structural repeat monomer (ED+Fn) but does not immunoreact with a plasma fibronectin monomer;
   (b) maintaining the admixture for a time period sufficient for said antibody to immunoreact with any ED+ Fn present in said sample and form an immunoreaction product;
   (c) determining the amount of the immunoreaction product formed in step (b), an elevated level of ED+ Fn present in said body sample being indicative of toxemia in said pregnant woman.

2. The method according to claim 1 wherein said antibody immunoreacts with an ED1 Type III repeat region.

3. The method of claim 1 wherein the antibody is polyclonal.

4. The method of claim 1 wherein the antibody is monoclonal.

5. The method according to claim 1 wherein said sample is from a pregnant woman in her first trimester of pregnancy.

6. The method according to claim 1 wherein said sample is from a pregnant woman in her second trimester of pregnancy.

7. The method according to claim 1 wherein said sample is from a pregnant woman in her third trimester of pregnancy.

8. The method according to claim 1 wherein the body sample is serum or plasma.

9. An assay method for determining the amount in a body fluid sample of fibronectin having an ED1 repeat region comprising the steps of:
   (a) admixing a predetermined amount of a body fluid sample from a pregnant woman with a solid support-affixed antibody to form a solid-liquid phase admixture, wherein said antibody immunoreacts with fibronectin having a 90 amino acid Type III structural repeat monomer (ED1+Fn) and does not immunoreact with a plasma fibronectin monomer;
   (b) maintaining said solid-liquid phase admixture for a predetermined time period sufficient for any ED1+Fn present in said sample to immunoreact with said solid support-affixed antibody to form a solid phase-bound immunoreaction product;
   (c) separating the solid and liquid phases formed in step (b); and
   (d) determining the amount of said separated solid phase-bound immunoreaction product formed in step (c), an elevated level of ED1+Fn present in said sample being indicative of toxemia in said pregnant woman.

10. The method according to claim 9 wherein the antibody is a polyclonal antibody and immunoreacts with at least one polypeptide having an amino acid residue sequence selected from the group consisting of:
   a) ELFPAPDGEEDTAELQC,
   b) ELFPAPDGEEDTAELQCGC,
   c) TYSSPEDGIHELFPAPDGEEDTAELQC, and
   d) TYSSPEDGIHELFPAPDGEEDTAELQCGC.

11. The method according to claim 9 wherein the antibody is monoclonal and immunoreacts with at least one polypeptide having an amino acid residue sequence selected from the group consisting of:
   a) ELFPAPDGEEDTAELQC,
   b) ELFPAPDGEEDTAELQCGC,
   c) TYSSPEDGIHELFPAPDGEEDTAELQC, and
   d) TYSSPEDGIHELFPAPDGEEDTAELQCGC.

12. The method according to claim 9 wherein said body sample is serum or plasma.

13. The method according to claim 9 wherein said body sample is from a pregnant woman in her first trimester of pregnancy.

14. The method according to claim 13 wherein said steps (a)–(e) are repeated at least once on a second body sample from said pregnant woman in her second trimester of pregnancy.

15. The method according to claim 9 wherein step (e) comprises:
   (i) admixing the immunoreaction product with a specific binding agent,
   (ii) maintaining the admixture under biological assay conditions for a time period sufficient for said specific binding agent to immunoreact with the immunoreaction product of step (c) to form a complex; and
   (iii) determining the amount of said complex.

16. The method according to claim 15 wherein the specific binding agent is a labeled antibody.

17. The method according to claim 16 wherein the label is an enzyme.

18. The method according to claim 17 wherein the enzyme is alkaline phosphatase.

19. The method according to claim 16 wherein the specific binding agent is a polyclonal anti-plasma fibronectin antibody conjugated to alkaline phosphatase.

* * * * *